United States Patent [19]

Warriner

[11] Plant 4,576

[45] Jul. 22, 1980

[54] ROSE PLANT

[75] Inventor: William A. Warriner, Tustin, Calif.

[73] Assignee: Jackson & Perkins Co., Medford, Oreg.

[21] Appl. No.: 19,311

[22] Filed: Mar. 12, 1979

[51] Int. Cl.[2] ..... A01H 5/00

[52] U.S. Cl. ..... Plt./20

[58] Field of Search ..... Plt./20

*Primary Examiner*—Robert E. Bagwill

*Attorney, Agent, or Firm*—Klarquist, Sparkman, Campbell, Leigh, Hall & Whinston

[57] ABSTRACT

A well branched, upright rose plant of the hybrid tea class with large flowers, Signal Red bloom color, blooms of 35 to 40 petals, and having very little fragrance.

6 Drawing Figures

1

BACKGROUND OF THE INVENTION

The present invention relates to a new and distinct variety of rose plant of the hybrid tea class which was originated by me by crossing the variety Baccara, U.S. Plant Pat. No. 1,367 with pollen of the variety South Seas, U.S. Plant Pat. No. 2,184.

The primary objective of this breeding was to produce a new rose variety of the hybrid tea class with the color similar to that of Baccara, primarily a greenhouse cut flower variety, but with larger blooms and better formed blooms. This objective was substantially achieved along with other desirable improvements as evidenced by the following unique combination of characteristics which are outstanding in this new variety and which distinguish it from its parents as well as from all other varieties of which I am aware:

1. A very vigorous, upright, well branched plant.
2. Most flowers on the flowering stems are borne singly with few side buds.
3. Fewer petals than its parent, Baccara.
4. Flower color in overall appearance is near Signal Red with a pronounced yellow area at point of attachment.
5. Very little fragrance.
6. Nearly round leaflets, similar in shape to those of Baccara.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:

*Seed parent.*—Baccara.

*Pollen parent.*—South Seas.

Classification:

*Botanical.*—Rosa hybrid.

*Commercial.*—Hybrid tea.

2

FLOWER

Observations made from specimens grown at Irvine, Calif., in September of 1978.

Blooming habit: Continuous.

Bud:

*Size.*—1¼ inches when petals start to unfurl.

*Form.*—Long, blunt top.

*Color.*—When sepals first divide near Blood Red (820) with darker shadings near midrib; when half blown, upper side of petals near Signal Red (719); lower side of petals Blood Red (820).

*Sepals.*—Color: Outer surface Scheeles Green (860/3) having numerous stipitate glands; inner surface heavily covered with white tomentum. Three appendaged sepals normally appendaged. Two unappendaged sepals, hairy edged.

*Hypanthium.*—Color: Scheeles Green (860/3). Shape: Funnel with distal end slightly smaller than the midsection. Size: Large. Surface: Smooth, glaucescent.

*Peduncle.*—Length: Short. Surface: Slightly glandular. Color: Light green. Strength: Stiff, erect.

*Opening.*—Outer petals curl out, mostly remaining nearly flat in full open stages.

Bloom:

*Size.*—Large. Average open size 4 inches.

*Borne.*—Mostly single.

*Stems.*—Long, strong.

*Form.*—When first open, high center.

*Petalage.*—Number of petals under normal conditions: 35 to 40.

*Color.*—Center of flower: Upper side of petals: Signal Red (719). Reverse side of petals: Near Blood Red (820). Base of petals: Small area at point of attachment Lemon Yellow (4). General tonality from a distance: Signal Red (719).

*Variegations.*—Occasionally a white streak in outer petals.

*Discoloration.*—First day: None. Third day: Little change. Color darkens slightly with age.

*Fragrance.*—Very slight.

Petals:

*Texture.*—Thick, leathery.

*Shape.*—Obovate.

*Form.*—Nearly flat.

*Arrangement.*—Imbricated. Petaloids, few.

*Persistence.*—Drop off cleanly.

*Lastingness.*—On the plant, long. As cut flower, long.

Reproductive parts:

*Stamens, anthers.*—Large, many. Color, Chinese Yellow (606). Arrangement, regular around styles.

*Filaments.*—Color: Red.

*Pollen.*—Gold yellow.

*Styles.*—Color: Red.

*Stigmas.*—Color: White.

PLANT

Form: Bush.

Growth: Very vigorous, upright, branching.

Foliage: Number of leaflets on normal mid-stem leaves 5 or 7.

*Size.*—Large.

*Quantity.*—Normal.

*Color.*—New foliage: Garnet Brown (00918/3). Old foliage: Near Spinach Green (0960/3).

Leaflets:

*Shape.*—Round to oval.

*Texture.*—Leathery.

*Edge.*—Serrated.

*Serrations.*—Single, small.

*Petiole.*—Rachis: Color, reddish. Underside: Prickles.

*Stipules.*—Long, bearded.

*Disease resistance.*—Normally resistant to mildew under normal growing conditions at Irvine, Calif.

Wood:

*New wood.*—Color: Reddish. Bark: Smooth.

*Old wood.*—Color: Green. Bark: Smooth.

Prickles:

*Quantity.*—On main stalks from base, ordinary. On laterals from stalk, ordinary.

*Form.*—Long base, hooked downward.

*Color when young.*—Red.

*Position.*—Irregular.

Small prickles:

*Quantity.*—On main stalks, few. On laterals, few.

*Color.*—Brown.

I claim:

1. A new and distinct variety of rose plant of the hybrid tea class, substantially as herein shown and described, characterized particularly as to novelty by the unique combination of its very vigorous, well branched, upright habit of growth, its primarily Signal Red flower color, blooms of 35 to 40 petals, and its very slight fragrance.

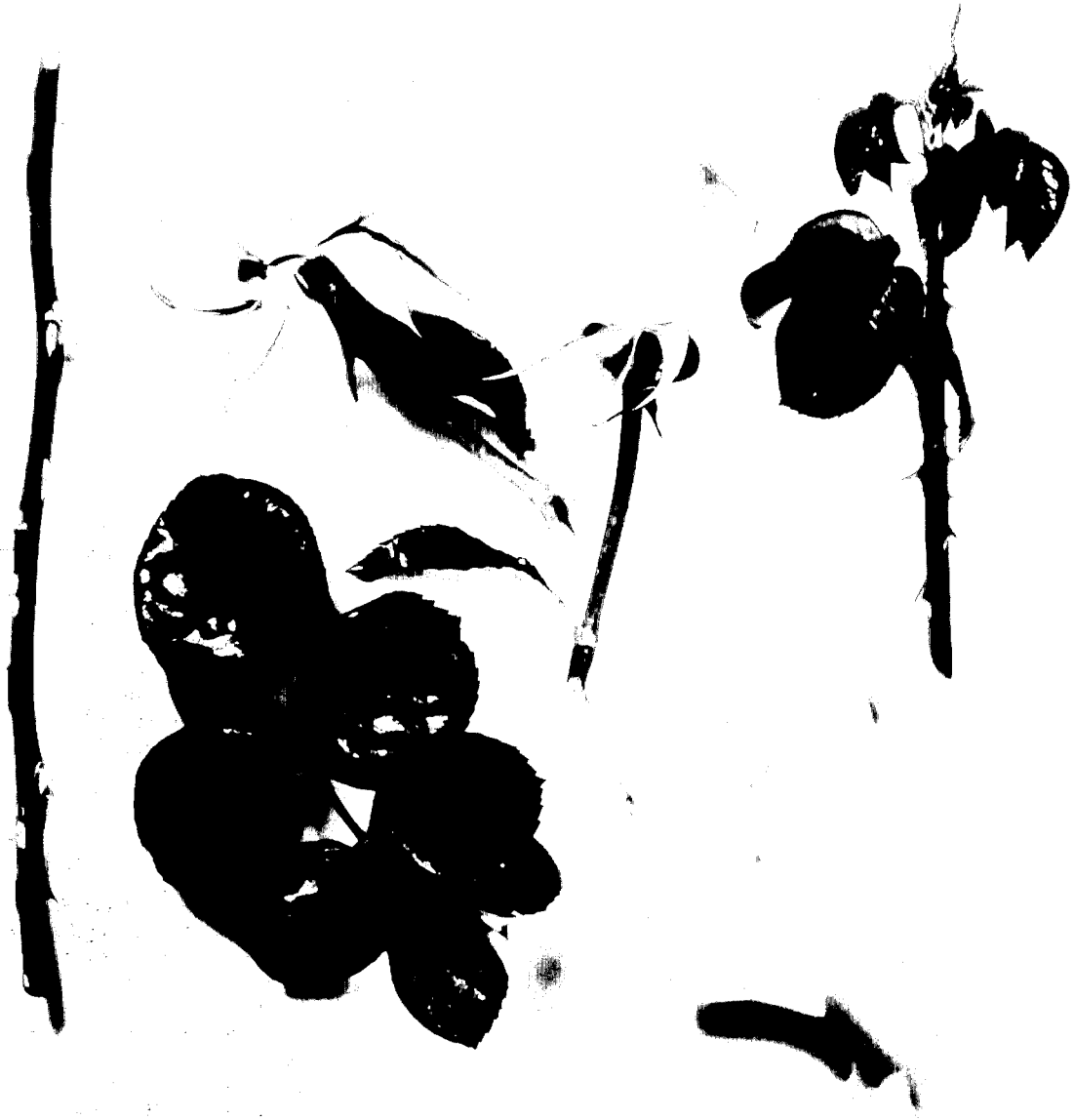

* * * * *